United States Patent [19]

McElwain et al.

[11] Patent Number: 5,171,685

[45] Date of Patent: Dec. 15, 1992

[54] **CLONING OF THE *BABESIA BOVIS* 60 KD ANTIGEN**

[75] Inventors: Terry F. McElwain, Pullman, Wash.; Stephen A. Hines, Gainesville, Fla.; Travis C. McGuire, Pullman, Wash.; Guy H. Palmer, Pullman, Wash.; Douglas P. Jasmer, Albion, Wash.; David W. Reduker, Pullman, Wash.; Will L. Goff, Moscow, Id.; Lance E. Perryman; William C. Davis, both of Pullman, Wash.

[73] Assignees: University of Florida, Gainesville, Fla.; The United States of America as represented by the United States Department of Agriculture, Washington, D.C.

[21] Appl. No.: 504,461

[22] Filed: Apr. 4, 1990

[51] Int. Cl.$^5$ .................. C12N 1/21; C12N 15/00; C12P 21/02; C12P 19/34

[52] U.S. Cl. ..................... 435/252.33; 435/69.3; 435/31; 435/172.3; 435/252.3; 435/320.1; 536/27; 530/350; 935/18; 935/31; 935/41; 935/58; 935/63; 935/73; 935/81

[58] Field of Search .............. 435/69.1, 69.3, 41, 435/172.3, 252.3, 252.8, 320.1, 235.1; 536/27; 530/350; 935/18, 31, 41, 58, 63, 73, 81

[56] References Cited

U.S. PATENT DOCUMENTS

4,762,711  8/1988  Buening et al. ................ 424/93

OTHER PUBLICATIONS

Gill et al Mol Biochem Parasitol. vol. 22 pp. 195–202 (1987).

Smith, D. D., M. A. James, M. Ristic, M. Aikawa, and C. A. Vega Y Murgula (1981) "Bovine Babesiosis: Protection of cattle with culture-derived soluble *Babesia bovis* antigen," Science 212:335–338.

Wright, I. G., B. V. Goodger, K. Rode-Bramanis, J. S. Matlick, D. F. Mahoney, and D. J. Waltisbuhl (1983) "The characterisation of an esterase derived from *Babesia bovis* and its use as a vaccine," Z. Parasitenkd. 69:703–714.

Wright, I. G., G. B. Mirre, K. Rode-Bramanis, M. Chamberlain, B. V. Goodger, and D. J. Mahoney (1985) "Protective vaccination against virulent *Babesia bovis* with a low molecular-weight antigen," Infect. Immun. 48:109–113.

Commins, M. A., B. V. Goodger, and I. G. Wright (1985) "Proteinases in the lysate of bovine erythrocytes infected with *Babesia bovis*: Initial vaccination studies," Int. J. Parasitol. 15:491–495.

Wright, I. G., and P. W. Riddles (1986) "Biotechnological Control of Tick-Borne Disease," Meeting of the Food and Agriculture Organization of the United Nations, Oct. 6–10, 1986, Rome, Italy, pp. 1–21.

Waltisbuhl, D. J., B. V., Goodger, I. G. Wright, G. B. Mirre, and M. A. Commins (1987) "*Babesia bovis*: Vaccination studies with three groups of high molecular weight antigens from lysate of infected erythrocytes," Parasitol. Res. 73:319–323.

Goff, W. L., W. C. David, G. H. Palmer, and T. C. Mcguire (1988) "Identification of *Babesia bovis* Merozoite Surface Antigens by Using Immune Bovine Sera and Monoclonal Antibodies," Infect. Immun. 56:2363–2368.

(List continued on next page.)

*Primary Examiner*—Joan Ellis
*Attorney, Agent, or Firm*—Saliwanchik & Saliwanchik

[57] ABSTRACT

The subject invention concerns the identification of novel merozoite surface proteins of *Babesia bovis*. Also disclosed are monoclonal antibodies to these proteins as well as genes which encode for the proteins.

The invention further concerns the use of the novel proteins, recombinant DNA clones, and monoclonal antibodies in the detection, treatment, and prophylaxis of babesiosis.

4 Claims, 7 Drawing Sheets

OTHER PUBLICATIONS

McElwain, T. F., L. E. Perryman, W. C. Davis and T. C. McGuire (1987) "Antibodies define multiple proteins with epitopes exposed on the surface of live *Babesia bigemina* merozoites," J. Immunol. 138(7):2298–2304.

Cowman, A. F., P. Timms, and D. J. Kemp (1984) "DNA polymorphisms and subpopulations in *Babesia bovis*," Mol. Biochem. Parasitol. 11:91–103.

Gill, A. C., A. F. Cowman, N. P. Stewart, D. J. Kemp, and P. Timms (1987) "*Babesia bovis*: Molecular and Biological Characteristics of Cloned Parasite Lines," Exp. Parasitol. 63:180–188.

Montenegro-James, S., M. Toro Benitez, E. Leon, R. Lopez, and M. Ristic (1987) "Bovine babesiosis: induction of protective immunity with culture-derived *Babesia bovis* and *Babesia begemina* immunogens," Parasitol. Res. 74:142–150.

Kuttler, K. L., M. G. Levy, M. A. James, M. Ristic (1982) "Efficac of a nonviable culture-derived *Babesia bovis* vaccine," Am. J. Vet. Res. 43(2):281–284.

| | | | | | |
|---|---|---|---|---|---|
| 1 | GAATTCAATG | CTTTTCTTAA | TGACAATCCT | CCACATATGT | TGACGAATGG |
| 51 | GAAAGAAAAA | ATGACTGAAT | ATTACAAAAA | AAATATATCC | AAGGAAGATG |
| 101 | GTGAGGTAAA | GGATTACAAA | ACTATGGTCA | AGTTTTGCAA | CGATTTTCTA |
| 151 | GACAGTAAAT | CTCCATTCAT | GAGACTATAT | AAGCATCTCA | ATGAATATGA |
| 201 | TGAGTTAGTG | AAGAAGAAGC | CAGCACAAGA | ATCTTCCCCT | GCTCCTTCAT |
| 251 | CCCCGCAAAG | ACCTGCTGAA | ACCCAACAAA | CTCAGGATTC | AGCTGCACCT |
| 301 | AGCACTCCCG | CAGCTCCCTC | ACCCCCGCAA | AGACCTGCTG | AAACCCAACA |
| 351 | AACTCAGGAT | TCAACTGCAC | CTGGCACTCC | CGCAGCTCCC | TCTCCTCAGG |
| 401 | GACCAACTGC | TGAAAGCCCA | TCCCAAGCTG | ACCACCCAAC | CAAACCTACT |
| 451 | CAGACACCTG | AAGGTAACCT | CCAAGGACAA | CAGGGTACAA | CCAAGCCAGC |
| 501 | CGGATCTTCA | TTCACCTATG | GCGGATTGAC | TGTGGCCACT | CTCTGCTACT |
| 551 | TCGTTCTCTC | TGCATTTTAA | TAACTAATGG | TAGTGACACA | ATAGTTTTGT |
| 601 | AAACTCATGT | TTTTAACTT | TTAATGAAATG | TAGTGTCTAC | AGTATTCGTG |
| 651 | GTACTTCGTC | AATAGTATAG | ACATATCTAC | AACAAGCAGA | GTACCAAAAG |
| 701 | TTATAAGCAA | TACTGTGCAC | GGCACAAACT | GTTTGTTATA | ACTTTGTCGT |
| 751 | TTCATTTAAC | AGAATACGTG | GTATATATTG | GAATCTCAGG | TAGTTCATAT |
| 801 | TCAATGTCAA | TGATAGCTGA | TTAATTTGTT | GTGGATATAA | CAGTGTGCGA |
| 851 | TTGCATTTCC | ATCTCTTGTA | ACATTGATAT | TTGATGGCAT | CAAAGAGAGA |
| 901 | TAGCTGCAAT | AGGCTAAGCA | AACAAAAGAA | TGGCTTTAAT | GGAAATAAAG |
| 951 | TTAAGCATAT | ATATCGTAAA | AATTAAAATA | CTAGCATATT | GCAGAATATA |
| 1001 | AACCTGCGTC | TGTTTAATTC | TTAACGAATA | AAAGTGAAAT | TGTAATACAC |
| 1051 | ATGTACATAC | GATAGATGGG | ATACATCCAC | ATGCGACCAT | ATAACGATGT |
| 1101 | GCGAATTTAG | TATATTTATA | TCAAACATGA | TGATGAAAGG | AAGGATTAGA |
| 1151 | AAATCAACAT | TTATAGTGCT | CAATTATATA | TGAATGCAAT | GTTGTGCTAC |
| 1201 | ACAGTTTGTC | AGAGGCCTGT | CAATGTGTAG | AATTC | |

FIGURE 1A

```
  1  EFNAFLNDNP PHMLTNGKEK MTEYYKKNIS KEDGEVKDYK TMVKFCNDFL
 51  DSKSPFMRLY KHLNEYDELV KKKPAQESSP APSSPQRPAE TQQTQDSAAP
101  STPAAPSPPQ RPAETQQTQD STAPGTPAAP SPQGPTAESP SQADHPTKPT
151  QTPEGNLQGQ QGTTKPAGSS FTYGGLTVAT LCYFVLSAF
```

FIGURE 1B

```
  1                       CTTCA ATCGTCCTTC CCGAAGGATC ATTCTACGAT
 36 GACATGTCTA AGTTCTACGG TGCTGTTGGA AGTTTCGACC AGACCAAATT
 86 GTATAGCGTT CTTTCTGCTA ACTTCAAAGC CGCTAAAATG GATGATCAGA
136 AGGTAAAAGA CACATTCAAA AATTTATACA AAGTCAACGC ATTGATAAAG
186 AACAATCCTA TGATTCGCCC TGATCTATTT AATGCAACTA TTGTTAGCGG
236 TTTTTCAACT AAGAATGACG AGGAAAAATT CAATGCTATA TTTGATTCCA
286 TTAAGGAAAT GTACTATAGA GCTCAACACA TGGACAAATA TTTGAAGTCA
336 CTAAGGTGGA ATACTGATAT TGTTGAGGAA GATCGTGAGA AGGCAGTTGA
386 ATATTCAAG AAGCATGTTT ATACGGGGGA ACACGTTGTT GACGTCAACG
436 GTATGGCTGG TGTTTGCAAG GAGTTTTTAA GCCCGGCCTC TGATTCTAC
486 AAACTTGTTG AGTCTTTTGA TGCGTTTGCA CATGCTAAGG TGCACGCTCA
536 AGTAGGAAAT TTTGTTAAAC CTGGAACTGA CATCGCTCCT CCTAAGGATG
586 TTACTGATGC ATTAGAAAAG GAATTGCAAG AGCAAAAACC TGCACGAAGT
636 GAGAGCACCG AAGTACCCGC TCCAGGTGAT GCATCTGGCG TCCAACAACC
686 GCCTGCATCA GGAACATCCC CGCAAGGACC TGCTCCGACT ACACCCAGCC
736 CATCTCCAGA GTCCCTCAGGA AACCTCCAAG GACAACAGGG TACAACCAAG
786 CCAGCCGGAT CTTCTTTCAC CTATGGCGGA TTGACTGTGG CTACTCTCTG
836 CTACTTCGTT CTCTCTGCAT TTTAAAAACT AATGGTAGTG ACACAATAGT
886 TTTGTAAACT CATGTTTTTT AACTTTTAAT ATGTAGTGAA AAA
```

FIGURE 2A

```
  1   SIVLP EGSFYDDMSK FYGAVGSFDQ TKLYSVLSAN FKAAKMDDQK
 46   VKDTFKNLYK VNALIKNNPM IRPDLFNATI VSGFSTKNDE EKFNAIFDSI
 96   KGMYYRAQHM DKYLKSLRWN TDIVEEDREK AVEYFKKHVY TGEHVVDVNG
146   MAGVCKEFLS PASDFYKLVE SFDAFAHAKV HAQVGNFVKP GTDIAPPKDV
196   TDALEKELQE QKPARSESTE VPAPGDASGV QQPPASGTSP QGPAPTTPSP
246   SPESSGNLQG QQGTTKPAGS SFTYGGLTVA TLCYFVLSAF
```

FIGURE 2B

```
   1 GACGGATAGT ATTTTACATA TACATTTGTC GACTTTTATA TATAGCAGTG
  51 CTATAGACAA ACAATACACA GATTAATCTT TAGATACTAA GTTCAATAAT
 101 ATTACGGACA TATTGTAGAC AATGAGAATC ATTAGCGGCG TTGTCGGTTG
 151 CCTTTTCTTG GTGTTTTCAC ACCATGTGTC TGCTTTTCGC CACAATCAGA
 201 GAGTAGGAAG TCTCGCTCCA GCTGAAGTGG TAGGTGATTT AACCTCCACA
 251 TTGGAAACAG CTGATACTTT GATGACTCTC CGTGACCACA TGCACAACAT
 301 TACTAAGGAT ATGAAACATG TTTGAGCAA TGGTCGTGAG CAGATTGTAA
 351 ATGATGTTTG CTCTAATGCT CCTGAGGACT CCAACTGTCG TGAGGTAGTT
 401 AACAATTATG CTGACCGTTG TGAAATGTAC GGATGCTTTA CGATTGACAA
 451 TGTCAAATAT CCGTTGTATC AAGAGTACCA ACCTCTATCT CTTCCAAACC
 501 CTTACCAGTT GGATGCTGCG TTCAGATTGT TGCATCGAAC TGCATCGAAC
 551 CCTGCCAAGA ACAGCGTAAA ACGCGAATGG TTGCGTTTCA GAAATGGAGC
 601 GAACCATGGT GATTACCACT ACTTCGTCAC TGGTCTGTTG AACAACAATG
 651 TTGTGCACGA GGAAGGAACT ACCGATGTTG AATATCTTGT CAACAAGGTA
 701 CTCTATATGG CTACAAGACT CTACAAGACT TATTTGACAG TAAACAGTAT
 751 GAACGCCAAG TTCTTCAACA GATTCAGCTT CACTACAAAG ATATTCAGTC
 801 GTCGTATTAG GCAAACATTG AGTGATATCA TCAGGTGGAA TGTTCCTGAA
 851 GATTTTGAAG AAAGGAGCAT CGAACGTATC ACTCAACTTA CTAGCAGCTA
 901 CGAAGATTAC ATGTTGACCC AGATTCCAAC TCTTTCCAAG TTTGCACGTC
 951 GTTATGCTGA CATGGTGAAG AAGGTTCTGC TCGGTAGCTT GACCTCGTAC
```

FIGURE 3-1

```
1001 GTTGAAGCTC CTTGGTACAA AAGATGGATA AAGAAATTCA GAGACTTTTT
1051 CTCTaaaAAC GTTACCCAAC CTACAAAGAA GTTCATCGAG GATACTAACG
1101 AAGTTACCAA AAACTATCTG AAGCCAATG  TTGCTGAGCC CACTAAAAAG
1151 TTTATGCAGG ACACTCACGA AAAAACCAAA GGCTATCTGA AAGAGAATGT
1201 AGCCGAACCT ACTAGACTT  TTTCAAGGA  GGCTCCTCAA GTCACCAAAC
1251 ACTTCTTCGA TGAGAACATT GGCCAACCCA CCAAGGAGTT TTTCAGGGAA
1301 GCTCCCCAAG CCACTAAaCA TTTCCTAGAC GAAAACATCG GTCAACCAAC
1351 CAAGGAGTTC TTCAGGGAGG CTCCTCAAGC CACTAAGCAC TTcCTAGGCG
1401 AGAATATTGC TCAACCTACT AAAGAATTTT TCAAGGATGT CCCTCAAGTC
1451 ACCAAGAAGG TTATAACTGA GAACATTGCT CAACCAACTA AGGAGTTCCG
1501 GAGGGAGGTT CCTCATGCTA CCATGAAAGT CTTGAATGAA AACATTGCTC
1551 AACCTGCCAA GGAAATCATA CATGAGTTTG GTACAGGCGC CAAGAATTTC
1601 ATTTCCGCAG CCCATGAAGG TACTAAGCAG TTCTTAAACG AAACTGTTGG
1651 CCAACCTACA AAGGAATTCC TGAACGGAGC TTTAGAAACT ACTAAAGACG
1701 CATTACACCA TCTGGGTAAA TCATCAGAAG AAGCCAACCT TTATGATGCC
1751 ACGAAAAATA CCACTCAGGC TAACGACTCA ACTACTTCCA ACGGTGAAGA
1801 CACCGCCGGA TACCTCTGAT GAGATGCGTT TATAATGGCA CAAACTCAAC
1851 AAATGATGTA TCGTCATCTG ATCCATCGGT TTTCAATATT GTATTGGATG
1901 CAATATCTGA ATGCATATGA TGCGACAGTT TCCATCATCG GGTGCCGAAT
1951 CGTAACTCTC ATAACACCAT TTTAAGTTAT GCTCGTGCCG
```

FIGURE 3-2

```
  1 MRIISGVVGC LFLVFSHHVS APRHNQRVGS LAPAEVVGDL TSTLETADTL
 51 MTLRDHMHNI TKDMKHVLSN GREQIVNDVC SNAPEDSNCR EVVNNYADRC
101 EMYGCFTIDN VKYPLYQEYQ PLSLPNPYQL DAAFRLFKES ASNPAKNSVK
151 REWLRFRNGA NHGDYHYFVT GLLNNNVVHE EGTTDVEYLV NKVLYMATMN
201 YKTYLTVNSM NAKFFNRFSF TTKIFSRRIR QTLSDIIRWN VPEDFEERSI
251 ERITQLTSSY EDYMLTQIPT LSKFARRYAD MVKKVLLGSL TSYVEAPWYK
301 RWIKKFRDFP SKNVTQPTKK FIEDTNEVTK NYLKANVAEP TKKFMQDTHE
351 KTKGYLKENV AEPTKTFFKE APQVTKHFFD ENIGQPTKEF FREAPQATKH
401 FLDENIGQPT KEFFREAPQA TKHFLGENIA QPTKEFFKDV PQVTKKVITE
451 NIAQPTKEFR REVPHATMKV LNENIAQPAK EIIHEFGTGA KNFISAAHEG
501 TKQFLNETVG QPTKEFLNGA LETTKDALHH LGKSSEEANL YDATENTTQA
551 NDSTTSNGED TAGYL
```

FIGURE 4

CLONING OF THE *BABESIA BOVIS* 60 KD ANTIGEN

CROSS-REFERENCE TO A RELATED APPLICATION

This application is a continuation-in-part of our co-pending application Ser. No. 333,155, filed Apr. 4, 1989.

BACKGROUND OF THE INVENTION

*Bovine babesiosis* is a tick-transmitted, hemoparasitic diease caused by intraerythrocytic protozoa belonging to the genus Babesia. The disease caused by Babesia manifests itself clinically by fever and extensive hemolytic anemia that often leads to hypotensive shock, cerebral involvement, and death. More than a half billion cattle are estimated to be at risk of acquiring babesiosis. This disease represents a primary impediment to food and fiber production in much of the world.

To date, control of bovine babesiosis in enzootic areas has been partially successful through vaccination with attenuated strains of Babesia spp. or with more virulent strains followed by chemotherapeutic control. Protective immunity in babesiosis may be directed against one or more surface antigens associated with sporozoites, infected erythrocytes, and/or merozoites. Merozoite surface antigens are important in the pathogenesis and immunology of babesiosis due to their role in the parasite's recognition of, attachment to, and penetration of host erythrocytes and their accessibility to the immune system.

Recently, progress has been made toward the identification and characterization of specific immunogens of merozoites of *Babesia bovis* (Smith, R. D., M. A. James, M. Ristic, M. Aikawa, and C. A. Vega Y Murgula [1981] Science 212:335-338; Wright, I. G., B. V. Goodger, K. Rode-Bramanis, J. S. Matlick, D. F. Mahoney, and D. J. Waltisbuhl [1983] Z. Parasitenkd. 69:703-714; Wright, I. G., G. B. Mirre, K. Rode-Bramanis, M. Chamberlain, B. V. Goodger, and D. J. Mahoney [1985] Infect. Immun. 48:109-113; Commins, M. A., B. V. Goodger, and I. G. Wright [1985] Int. J. Parasitol. 15:491-495; Wright, I. G. and P. W. Riddles [1986] "Biotechnological Control of Tick-Borne Disease," Meeting of the Food and Agriculture Organization of the United Nations, 6-10 Oct. 1986, pp. 1-21, Rome, Italy; Waltisbuhl, D. J., B. V. Goodger, I. G. Wright, G. B. Mirre, and M. A. Commins [1987] Parasitol Res. 73:319-323; Goff, W. L., W. C. Davis, G. H. Palmer, and T. C. McGuire [1988] Infect. Immun. 56:2363-2368) and *Babesia bigemina* (McElwain, T. F., L. F. Perryman, W. C. Davis, and T. C. McGuire [1987] J. Immunol. 138(7):2298-2304). However, in only one instance (Smith et al., 1981) were antigens which provided protection against infection determined to be surface-exposed on merozoites as opposed to cytoplasmic in location.

Bovine babesiosis can be caused by either *Babesia bigemina* or *Babesia bovis*. These parasites have antigenic similarities and differences that may have important functional roles in the induction of protective immunity and antibody-based diagnosis. Also, *B. bovis* isolates, including the current Australian vaccine strain, are now known to consist of subpopulations that vary antigenically, in virulence, and in abundance within an isolate (Cowman, A. F., P. Timms, and D. J. Kemp [1984] Mol. Biochem. Parasitol. 11:91-103; Gill, A. C., A. F. Cowman, N. P. Stewart, D. J. Kemp, and P. Timms [1987] Exp. Parasitol. 63:180-188).

Current vaccine strategies include the use of attenuated live *Babesia bovis* parasites and various inactivated preparations (Montenegro-James, S., M. Toro Benitez, E. Leon, R. Lopez, and M. Ristic [1987] Parasitol. Res. 74:142-150; Smith et al., 1981; U.S. Pat. No. 4,762,711 issued to Buening et al.; Kuttler, K. L., M. G. Levy, M. A. James, M. Ristic [1982] Am. J. Vet. Res. 43(2):281-284). The attenuated vaccine provides the best protection against challenge with both homologous and heterologous strains, although there are a number of serious disadvantages, including a short shelf-life, variation in virulence, contamination with host erythrocyte stroma, and perpetuation of the life cycle by creation of a carrier state. Inactivated vaccines induce protection against challenge with homologous strains; however, only partial protection occurs against challenge with heterologous strains.

Animals that survive natural field infection or that recover from infection with an attenuated vaccine strain are protected against clinical disease. However, premunization in this manner is expensive, impractical in developing countries that lack the necessary infrastructure, and a potential mode of transmission for other blood-borne diseases.

BRIEF SUMMARY OF THE INVENTION

Disclosed and claimed here are novel merozoite proteins of *Babesia bovis*. These proteins are known to be expressed on the surface of the merozoite and may be used to raise neutralizing antibodies. Thus, they can be used in the formulation of subunit vaccines for the prophylaxis of bovine babesiosis. Several of the proteins described here raise antibodies to both *Babesia bovis* and *Babesia bigemina*, while others are species, or even isolate, specific.

Also disclosed are monoclonal antibodies to bovine babesiosis antigens. These monoclonal antibodies are used to identify merozoite surface antigens and may be used in the treatment and/or diagnosis of bovine babesiosis.

A further element of the invention is the identification of genes which code of Babesia proteins. These genes can be used to make recombinant proteins which can be utilized for vaccines.

The invention also provides a means of detecting the presence of disease-causing Babesia organisms. The detection method involves the use of DNA probes which selectively identify the presence of these organisms.

BRIEF DESCRIPTION OF THE DRAWINGS

FIG. 1A is the DNA sequence of lambda-Bo44.

FIG. 1B is the amino-acid sequence of lambda-Bo44 in the single-letter designations.

FIG. 2A is the DNA sequence for rBv42.

FIG. 2B is the amino acid sequence for rBv42 in the single-letter designations.

FIG. 3-1 through 3-2 is the DNA sequence for rBv60.

FIG. 4 is the amino acid sequence for rBv60 in the single-letter designations.

DETAILED DESCRIPTION OF THE INVENTION

The subject invention pertains to the identification of surface-exposed proteins of *B. bovis* merozoites. The proteins of the invention have sizes of 16, 25, 37, 42, 44, 55, 60, 85, 98, 125, 145, 225, and 250 kDa. The evidence that the proteins are surface exposed includes: (i) monoclonal antibody binding of live merozoites, (ii) labeling by surface iodination, and (iii) sensitivity to mild trypsinization.

We have identified *B. bovis* merozoite proteins that, by virtue of their surface location and their reactivity with immune bovine sera, are candidates for subunit vaccines. Among the numerous proteins recognized by immune bovine sera, six proteins (37, 42, 55, 85, 125, and 145 kDa) appeared to be relatively immunodominant.

The 145 kDa protein was of parasite origin, but its location on the membrane surface was not directly apparent. This protein may have a small portion exposed at the surface of the merozoite that is sensitive to mild trypsinization but the epitope recognized by the monoclonal antibody located internally.

Immunoprecipitation of radiolabeled antigens with bovine antisera indicated that many *Babesia bovis* merozoite proteins contain isolate-common epitopes, while at least 8 *B. bovis* proteins contain species-cross-reactive epitopes. The amino acid sequence of three of the immunogenic proteins from *B. bovis* (42 kDa) have been determined. Amino acid sequences which deviate in insignificant ways from the disclosed amino acid sequences fall within the scope of the subject invention so long as the antigenic properties of the protein are not altered. Thus, the subject invention includes mutants and fragments of the amino acid sequences depicted herein which do not alter the protein secondary structure, or if the structure is altered, the antigenic activity is retained. In particular, it should be understood that conservative substitutions of amino acids may be made. For example, amino acids may be placed in the following classes: basic, hydrophobic, acidic, polar, and amide. Substitutions whereby an amino acid of one class is replaced with another amino acid of the same type fall within the scope of the subject invention so long as the substitution does not materially alter the antigenic activity of the compound.

The ability of antibodies against heterologous geographic isolates to immunoprecipitate proteins from the Mexico *B. bovis* isolate indicates the conservation of at least one and probably more epitopes between proteins from the heterologous isolates. The conservation of these epitopes is extensive, as many Mexico *B. bovis* isolate proteins were precipitated by antisera against a different geographic isolate (Honduras). The 42,000 molecular weight Mexico *B. bovis* protein was precipitated by all five of the undiluted and three of the diluted Honduras antisera.

Among the highly immunogenic *B. bovis* proteins, only one (the 42,000 molecular weight protein) is both isolate common and species specific. This protein can be used as an antigen for species-specific, antibody-based diagnosis.

Monoclonal antibodies (MoAbs) were generated against surface-exposed proteins on merozoites of *B. bovis*. A genomic library constructed in the lambdagt11 expression vector was screened with MoAbs for identification of clones expressing recombinant surface proteins. Four recombinant clones were identified.

Southern blot analyses confirmed the parasite-specificity of the cloned inserts. Western blot analyses demonstrated that recombinant protein production in these clones is IPTG-induced and that the recombinant molecules exist as beta-galactosidase fusion proteins.

Additionally, recombinant proteins, partially purified by affinity column chromatography and gel filtration chromatography, reacted with specific MoAbs in Western blot assay indicating that the integrity of the epitopes is retained during purification. Calves immunized with these partially purified recombinant proteins developed titers of between $10^{-2}$ and $10^{-5}$ as evidenced by IFA-live. Immune sera from these animals immunoprecipitated metabolically-radiolabeled merozoite proteins confirming that determinants found on native proteins are expressed by the clones.

DNA probe candidates were also identified using the lambda-gt11 genomic library of *B. bovis*. Two DNA sequences, designated lambda-BO6 and lambda-Bo25, hybridized to Babesia DNA but not to bovine DNA. Bo6 detected Mexico and Australia isolates of *B. bovis* as well as *B. bigemina* DNA. Lambda-Bo25 demonstrated greater specificity; it did not hybridize detectably to *B. bigemina* DNA and showed greater sensitivity for Mexico isolates of *B. bovis* than for Australia isolates.

Thus, lambda-Bo6 is a good candidate for detecting Babesia infections in cattle and ticks, and lambda-Bo25 can be used to distinguish geographic isolates of *B. bovis*.

Materials and Methods

Strain of *B. bovis*, Stabilate Preparation, Cryopreservation, and In Vitro Cultures. The strain of *B. bovis* used in experiments outlined herein was originally isolated from a *Boophilus microplus* tick-induced infection in Mexico by Dr. R. D. Smith, University of Illinois at Urbana (Goff, W. L. and C. E. Yunker [1986] Exp. Parasitol. 62:202-210). The cloned line was derived from the Mexico isolate by limiting dilution cloning as previously described by Rodriguez et. al. (Rodriguez, S. D., G. M. Buening, T. J. Green, and C. A. Carson [1986] Infect. Immun. 42:15-18). The parasites have been maintained in our laboratory by either repeated passages in splenectomized Holstein-Freisian bull calves or in vitro cultivation. Cryopreservation of stabilates of *B. bovis*-infected erythrocytes obtained from infected calves and the preparation of partially purified merozoites from thawed stabilates has been described (Palmer, D. A., G. M. Buening, and C. A. Carson [1982] Parasitol 84:567; McElwain, T. F., L. E. Perryman, W. C. Davis, and T. C. McGuire [1987] J. Immunol. 138:2298-2304). Continuous in vitro cultivation of *B. bovis* was performed using a modification of the microaerophilous stationary phase (MASP) culturing system (Goff and Yunker, 1986). Viability of merozoites obtained from either frozen stabilates or in vitro cultivation was confirmed by 6-CFDA assay (McElwain et al., 1987) prior to their use in experiments or immunizations.

Isolation of Merozoites. Merozoites were harvested from cultures after the relative percentage of parasitized erythrocytes was increased by sequential reduction of the concentration of erythrocytes (Goff and Yunker, 1986). For collection of merozoites, the contents of flasks containing >15% parasitized erythrocytes were centrifuged at 400×g for 10 min at 4° C. The supernatant was centrifuged at 3,000×g for 15 min at 4° C. to pellet the merozoites. The merozoites were suspended in Puck saline-glucose (saline-G), and 2 ml was overlaid on 10 ml of a preformed continuous gradient of 65% Percoll-35% Puck saline-G. The gradient was centrifuged in a swinging bucket rotor at 3,000×g for 20 min at 4° C. The merozoites were isolated from a band with an approximate density of 1.069 g/ml between erythrocyte ghosts at the Percoll-Puck saline-G interface and the residual intact erythrocyte pellet. The merozoites were washed once in 0.15M NaCl containing 0.01M sodium citrate (CS), suspended in CS, and stored on ice until used (within 2 to 4 hr).

Purification, Quantitation and Viability Estimation of Merozoites. An equal volume of the isolated merozoite suspension was mixed with 6-carboxy fluorescein diacetate (6-CFDA; final concentration in CS, 10 ug/ml; Calbiochem-Behring, La Jolla, CA) (McElwain et al., 1987). The mixture was incubated at room temperature for 20 min, followed by centrifugation at $1,000 \times g$ for 10 min and was then suspended in phosphate-buffered saline (PBS; 0.15M, pH 7.2) for counting on a hemacytometer. The sample was examined with phase microscopy and epifluorescence with a 40X oil objective and fluorescein filter (450 to 520 nm). Viability was assessed as the percentage of total merozoites emitting fluorescence.

Preparation of Immune Bovine Sera. Two spleen-intact Holstein-Freisian steers, 14 months of age and indirect fluorescent-antibody test negative for *B. bovis*, *B. bigemina*, and *Anaplasma marginale*, were inoculated intravenously with approximately $6 \times 10^8$ *B. bovis*-infected erythrocytes from the same blood stabilate used to initiate in vitro cultures. On day 9 postinoculation each steer developed detectable parasitemia and a febrile response which persisted through day 13 postinoculation. Antibody specific for *B. bovis* was detected with the indirect fluorescent-antibody test on day 10 postinoculation. The steers were challenge inoculated as before on days 48 and 80 postinoculation, and although the animals did not develop a fever or parasitemia, the antibody titer increased after each challenge. Sera were collected and stored at $-70°$ C. after the final challenge, when the indirect fluorescent-antibody test titer was 1:10,000.

In addition, the cloned line was passed through a splenectomized calf whose blood at peak parasitemia was used to infect five 4–5 month old Holstein steers ($5 \times 10^7$ infected erythrocytes each) and to initiate in vitro cultures. The cattle were reinfected at 23 days post infection (DPI) with $10^8$ infected erythrocytes (iRBC) from another splenectomized calf and at 77 and 99 DPI with $10^8$ iRBC from culture. At day 127, the five cattle and three weight-matched, previously uninfected controls were infected with $10^9$ iRBC from culture. The packed cell volume (PCV) of all animals was monitored daily.

Immunofluorescence of Live Merozoites. Viable merozoites were collected as described above and reacted with the various antibodies by a previously described technique (McElwain et al. [1987], supra). The MoAb-containing ascites fluids were diluted 1/10 (40 ug/ml) in PBS. Immune bovine sera were diluted 1/10 in PBS. An equal volume of each antibody preparation was added to 100 ul of a merozoite suspension and incubated on ice for 1 hr. Each sample was centrifuged at $3,000 \times g$ for 10 min, and the merozoites were washed twice in cold PBS. The samples were then suspended in the appropriate rhodamine-conjugated second antibody (1/40 dilution in PBS) (Kirkegaard and Perry, Inc., Gaithersburg, MD) and incubated on ice for 1 hr. After being washed, the merozoites were suspended in 6-CFDA and incubated for 20 min at room temperature. The merozoites were then centrifuged at $3,000 \times g$ for 10 min at 4° C., suspended in 50 ul of PBS, and examined in wet mounts with appropriate filters for rhodamine (antibody binding) and fluorescein (6-CFDA viability) (546 to 590 nm and 450 to 520 nm, respectively).

Surface Radioiodination. Purity of the gradient separated merozoites was also examined by direct light microscopy of Giemsa stained smears and by transmission electron microscopy of selected samples fixed in 2% v/v glutaraldehyde in 0.1M potassium phosphate buffer containing 1% w/v sucrose. Parasites were often arranged in clumps and mixed with very rare erythrocyte ghosts ($<0.1\%$). Merozoites were surface radioiodinated by a previously described lactoperoxidase catalyzed method (Palmer, G. H., and T. C. McGuire [1984] J. Immunol. 133:1010–1015).

Donor erythrocytes (nRBC) from uninfected control cultures were collected, washed three times in PBS, and radiolabeled identically. An equivalent number of nRBC ghosts were prepared by lysing washed uninfected cells from control cultures by freeze/thaw in liquid nitrogen. Ghosts were washed free of hemoglobin in PBS by centrifugation at $35,000 \times g$, 20 min, 4° C. and discarding the supernatant until it was clear. The final pellet was resuspended in PBS for radioiodination by lactoperoxidase.

Metabolic Radiolabeling of Merozoites. Metabolically radiolabeled parasite proteins from calf-derived merozoites were prepared for use in immunoprecipitation experiments according to the methods of McElwain et al. (1987, supra) except that cultures containing 100 uCi of [$^{35}$S]-methionine ($^{35}$S-Met; New England Nuclear, Boston, MA) per $3 \times 10^9$ erythrocytes were incubated at 37° C. for 8–9 hr in a Forma Scientific water jacketed incubator instead of a candle jar. Parasites cultivated in vitro were metabolically radiolabeled using normal growth medium (Goff and Yunker, 1986) or D,L-methionine-free medium, addition of 20–400 uCi/ml $^{35}$S-Met, $^3$H-myristic acid, or $^3$H-glucosamine, and incubation of cultures for 12–20 hr at 37° C. Erythrocytes containing radiolabeled merozoites were solubilized in lysis buffer, TCA-precipitable radioactive counts were determined by a filter paper technique (New England Nuclear), and samples were frozen at $-70°$ C. until used.

Phase Separation in TRITON ™ X-114. Washed iRBC's from $^{35}$S-methionine labeled cultures were lysed in 10 mM Tris, 154 mM NaCl pH 7.4, 1% (v/v) TRITON ™ X-114, 1 mM phenylmethylsulfonyl fluoride (PMSF) at 0°–4° C. and frozen at $-20°$ C. For protein separation, the antigen extract was first processed as described for immunoprecipitation. $10^7$ protein bound counts per minute (CPM) in a volume of 2.0 ml was laid over a 2.0 ml cushion of 6% (w/v) sucrose, 10 mM Tris, 154 mM NaCl, 1 mM PMSF in a 15 ml conical tube (Bordier, C. [1981] Exp. Parasitol. 20:125–129). The tube was incubated at 37° C. for 5 min to allow clouding of the protein extract and then centrifuged at $750 \times g$ at room temperature for 5 min in a swinging bucket rotor. The detergent phase was seen as a thick, oily 100–200 ul pellet and the overlying aqueous phase and sucrose cushion were each removed to separate tubes. The phase separation was repeated twice by adding 200 ul of 15% (v/v) TRITON ™ X-100 in 10 mM Tris, 154 mM NaCl to the aqueous phase, dissolving the detergent on ice, and re-extracting at 37° C. over the same sucrose cushion. The three detergent phases resulting from centrifugation were mixed with 10 mM Tris, 154 mM NaCl at 0°–4° C., combined, and TCA-precipitable radioactivity counted along with the aqueous phase.

Immunoprecipitation. Immune sera were used either unadsorbed or adsorbed three times with an equal volume of packed intact nRBC's and three times with an equal volume of nRBC ghosts. Radiolabeled *B. bovis* or bacterial lysate was processed as described previously (Palmer and McGuire [1984], supra) and incubated overnight at 4° C. with 15 ul of bovine serum or 15 ul of serum diluted in Veronal buffered saline (VBS) pH 7.4, 1% (v/v) Nonidet P-40 (NP-40). 150 ul of 10% (v/v) formalinized Protein G-bearing Streptococcus (Omnisorb, Calbiochem, San Diego, Calif.) in VBS pH 7.4, 1% (v/v) NP-40, 0.1% (w/v) gelatin was added and incubated for 2 hr at 4° C. (Akerstrom, B., T. Brodin, K. Reis, and L. Bjorck [1985] J. Immunol. 135:2589–2592). The precipitates were washed twice with VBS, 1% (v/v) NP-40; four times with VBS, 2M NaCl, 1% (v/v) NP-40, 10 mM ethylenediaminetetraacetic acid (EDTA); and twice more with VBS, 1% (v/v) NP-40. Alternatively, 5 ul of bovine serum, 10 ul of rabbit serum, or 5 ug monoclonal antibody were incubated for 30 minutes at 4° C. with radiolabeled lysate. Rabbit anti-bovine or rabbit anti-mouse immunoglobulin sera were added and incubated for 30 minutes at 4° C., followed by 10% v/v protein-A-bearing *Staphylococcal aureus* for 30 minutes at 4° C. Immune complexes were washed seven times with TEN buffer (20 mM Tris-HCl, 5 mM EDTA, 0.1 mM NaCl, 15 mM NaN$_3$,pH 7.6) containing Nonidet P-40, and for the second through fifth washes, 2M NaCl, by centrifuging at 1250× g. The precipitated protein was eluted by a described method and either frozen at −20° C. or loaded directly onto a polyacrylamide gel (Palmer and McGuire [1984], supra).

Sodium Dodecyl Sulfate Polyacrylamide Gel Electrophoresis (SDS-PAGE) of Immunoprecipitates and Autoradiography. Immunoprecipitates were electrophoresed under reducing conditions in 7.5 to 17.5% continuous gradient polyacrylamide gels (Takac, B. [1979] In: *Immunological Methods*. T. Lefkovitz and B. Persin, eds., p. 81, Academic Press, New York). $^{14}$C-labeled protein standards used for molecular weight determination were myosin, 200 kDa; phosphorylase b, 92.5 kDa; bovine serum albumin, 69 kDa; ovalbumin, 46 kDa; carbonic anhydrase, 30 kDa; and lysozyme, 14.3 kDa (Amersham Corp., Arlington Heights, Ill.). For $^{125}$I-labeled antigens, gels were fixed in 30% (v/v) methanol, 10% (v/v) acetic acid, vacuum dried, and exposed to Kodak XAR-2 X-ray film with an intensifying screen at −70° C. For $^3$H and $^{35}$S-labeled immunoprecipitates, gels fixed in 30% (v/v) methanol, 10% (v/v) acetic acid, 10% (w/v) trichloroacetic acid (TCA) were impregnated with En$^3$Hance (New England Nuclear Corp., Boston, Mass.) prior to drying and exposure to X-ray film at −70° C. (Palmer and McGuire, 1984).

Immunoblotting. Immunoblotting of merozoite and recombinant lysogen proteins using monoclonal antibodies was performed as outlined (McElwain et al., 1987) using standard procedures (Towbin, H. and J. Gordon [1984] J. Immunol. Methods 72:313–340). Parasite antigen for immunoblotting was prepared from MASP culture flasks with approximately 25% parasitemia. Briefly iRBC's and nRBC controls were collected, washed two times in cold Puck's saline-G and two times in cold PBS, resuspended in PBS, counted, and frozen at −20° C. To remove hemoglobin from lysed cells, the samples were thawed and washed in cold PBS (43,000× g, 20 min, 4° C.) until the discarded supernatant was clear. The final pellet was extracted in lysis buffer, processed identically to radiolabeled antigen for immunoprecipitation, and aliquoted for freezing at −20° C. A volume corresponding to 2.5×10$^7$iRBC's or an equivalent total number of nRBC's (10$^8$) was mixed with 3X SDS-PAGE sample buffer, boiled for 3 minutes, electrophoresed in a 7.5 to 17.5% continuous gradient polyacrylamide gel, and then electrophoretically transferred overnight to a nitrocellulose membrane (Towbin and Gordon, 1984). Immunoblotting using bovine antisera was performed as follows: The nitrocellulose was washed three times quickly in VBS pH 7.4, 0.25% (v/v) TWEEN ™ 20, 0.25% (w/v) gelatin (blocking buffer), incubated 4–6 hr in blocking buffer, cut into strips, and each strip reacted overnight at room temperature with immune serum diluted in blocking buffer. The nitrocellulose strips were then washed three times in blocking buffer and two times in VBS 0.1% (w/v) gelatin prior to incubation for 2 hours at room temperature with $^{125}$I-Protein G (Amersham Corp.) in VBS pH 7.4, 0.1% (w/v) gelatin (Akerstrom, B., T. Brodin, K. Reis, and L. Bjorck [1985] J. Immunol. 135:2589–2592). The strips were washed twice with VBS 0.1% (w/v) gelatin and four times with 1M NaCl, 10 mM EDTA, 0.25% (v/v) TWEEN ™ 20. They were then air-dried, taped to cardboard, and exposed to X-ray film with an intensifying screen at −70° C.

Dot Blot Immunoassay. Because MoAbs were used to screen the lambdagt11 genomic library for clones expressing recombinant surface proteins, they were first evaluated for their ability to bind native antigen applied to nitrocellulose filters. 6-CFDA-positive merozoites were obtained from frozen blood stabilates, lysed in buffer containing 50 mM Tris, 5 mM EDTA, 5 mM iodoacetamide, 1 mM PMSF, 0.1 mM N-alpha-p-tosyl-L-lysyl chloromethyl ketone (TLCK) and 1% NP-40 (lysis buffer), and frozen at −70° C. until use. Aliquots of 1 ul containing either 10$^7$, 10$^6$ or 10$^5$ merozoites were spotted onto nitrocellulose filters and air dried. Corresponding numbers of similarly lysed noninfected bovine erythrocytes were spotted on for control. Nitrocellulose filters with spotted antigen were washed three times (10 min each) in buffer containing 10 mM Tris (pH 8.0), 150 mM NaCl, 0.05% TWEEN ™ 20, and 0.1 mM PMSF (TNTP) then incubated in TNTP with 5% nonfat dry milk for 1 hr to block unbound sites. Filters were washed three times in TNTP plus 5% milk, incubated in the same buffer containing 2 ug/ml of specific surface-binding MoAb ($\frac{1}{2}$ hr), washed three times, incubated for $\frac{1}{2}$ hr in a 1:5000 dilution of rabbit anti-mouse immunoglobulin (prepared in our laboratory) in TNTP plus 5% milk. After three washes, the filters were incubated for $\frac{1}{2}$ hr in TNTP plus 5% milk containing 5×10$^6$ CPM of $^{125}$I-labeled Protein A, washed sequentially with TNTP, TNTP plus 0.1% TRITON ™ X, and TNTP, then dried and examined by autoradiography.

Following are examples which illustrate procedures, including the best mode, for practicing the invention. These examples should not be construed as limiting. All percentages are by weight and all solvent mixture proportions are by volume unless otherwise noted.

Example 1-Generation of Monoclonal Antibodies Against Surface Epitopes

Partially purified merozoites of *B. bovis* obtained from frozen blood stabilates were used to immunize BALB/c mice for hybridoma production. Each mouse received an initial subcutaneous immunization of 10$^7$ 6-CFDApositive organisms in Freund's complete adjuvant followed by 3-4 subcutaneous immuniations of $10^7$ 6-CFDA-positive organisms in Freund's incomplete adjuvant at 2-4 week intervals. Mouse serum was titered by IFA-live (Barbet, A. F. and T. C. McGuire [1978] Proc. Natl. Acad. Sci. USA 75:1989-1993) after the last immunization, and mice with high titers ($\geq$1:1000) received an intravenous booster immunization of $10^6$ 6-CFDA-positive organisms in sterile PBS. Three days later the mice were killed and their spleen cells fused to SP2/0 myeloma cells using standard procedures (McGuire, T. C., L. E. Perryman, and W. C. Davis [1983] Amer. J. Vet. Res. 44:1284-1288). Hybridoma supernates were screened first for convenience by IFA-fixed (Ross, J. P. J and K. F. Lohr [1968] Res. Vet. Sci. 9:557-562). Positive supernates were then screened by IFA-live using stabilate-derived merozoites in order to identify surface reactive MoAbs (McElwain et al. [1987]). The MoAbs were first screened on fixed infected erythrocyte preparations, and four MoAbs were selected for further evaluation because of their distinctive patterns of fluorescence. These patterns included staining of the merozoite cytoplasm and membrane (BABB35A4), merozoite membrane (BABB90C4), and merozoite cytoplasm (BABB93A1) and a single, punctate reaction appearing polar in location on merozoites (BABB75). The four MoAbs all retained their original specificities after the hybridoma cells were cloned twice and used to produce ascites fluids.

Example 2-Immunoprecipitation of Surface Radioiodinated and Metabolically Radiolabeled Proteins Spontaneously released merozoites for surface binding and labeling experiments were isolated on Percoll gradients. A large proportion retained their surface coat and >80% were viable, as determined by 6-CFDA staining. On three occasions, $10^8$ of these isolated merozoites were inoculated intravenously into susceptible, splenectomized calves. In each case, infection was achieved with a prepatent period similar to that in calves that received an equivalent number of infected erythrocytes from a blood stabilate. Also, in vitro cultures have been routinely reestablished after introduction of these isolated merozoites.

Radioiodinated merozoite preparations were immunoprecipitated with the MoAbs described above to confirm the outer surface or cytoplasmic location of the reactive epitopes. BABB35A4 precipitated a major protein of 42 kDa and a minor protein of 37 kDa. BABB75 and BABB90C4 precipitated single proteins of 60 and 85 kDa, respectively.

To determine which parasite proteins were recognized by the bovine immune system, we used twofold serial dilutions of immune bovine sera to immunoprecipitate metabolically labeled preparations. Proteins with relative molecular masses ranging from approximately 16 to >200 kDa were recognized by the immune bovine sera. Among the proteins recognized were those identical in molecular mass to those precipitated by BABB35A4 (42 and 37 kDa), BABB75 (60 kDa), and BABB93A1 (145 kDa). In addition, proteins of 145, 42, 120 and 75 kDa appeared to be immunodominant, as they were precipitated by immune bovine sera at the greatest dilution tested.

Example 3-Further Identification of Merozoite Surface Proteins

Subinoculation of $5\times10^7$ infected erythrocytes (iRBC) of a cloned B. bovis line from a splenectomized calf into 4-5 month old cattle caused a 39% reduction in packed cell volume (PCV) (range 31-47). Calves were re-infected three times with approximately $10^8$ iRBC of the cloned isolate and then challenged with $10^9$ iRBC in concert with three previously uninfected control animals. Only the initial infection caused a significant reduction in PCV when compared to the PCV during the week prior to each infection. Control cattle in the final challenge experiment experienced a 28% reduction in PCV (p< or =0.0005 when compared to previously infected cattle; Student's paired t test).

Merozoites spontaneously released from culture and purified on Percoll gradients were 95-100% viable by 6-CFDA staining. In all five animals, immunoprecipitation of surface radioiodinated proteins with immune sera that had been extensively adsorbed against donor erythrocytes (nRBC) and erythrocyte ghosts identified seven dominant surface proteins with relative molecular weights of 250, 125, 98, 85, 55, 42, and 37 kilodaltons. The 250 kDa protein does not enter the resolving gel in a standard 14 cm 7.5-17.5% polyacrylamide gel but is clearly resolved in a 25 cm gel. An eighth protein of 25 kDa is immunoprecipitated by immune sera from two calves. Control immunoprecipitation of identically radioiodinated intact nRBC and nRBC ghosts revealed no specific bands on SDS-PAGE.

Adsorbed immune sera was used to immunoprecipitate $^{35}S$-methionine metabolically labeled parasite proteins which were run alongside immunoprecipitated surface-iodinated merozoite proteins in a polyacrylamide gel. The immunoprecipitable $^{35}S$ antigen profile is identical in all five protected animals. The 125, 98, 85, 55, 42, and 37 kDa antigens comigrate perfectly with metabolically labeled proteins. The 25 kDa surface protein that is not identified by immunoprecipitation of methionine labeled antigen does comigrate with a glycoprotein that is metabolically labeled with $^3H$-glucosamine. An $^{35}S$-methionine labeled 25 kDa protein can be precipitated from other $^{35}S$-antigen preparations.

Example 4-Immunogenicity

While the reactivity of immune sera against the majority of $^{35}S$-labeled proteins can be diluted out, sequential serum dilutions (1:160-1:640) selectively precipitate the 125, 55, and 42 kDa proteins that were also surface labeled. Because this method is dependent on the specific radioactivity of labeled proteins, dilute sera was also examined for its ability to react with parasite antigens by immunoblotting. Compared to undiluted serum, immune sera diluted 1:500 recognizes a limited number of blood stage proteins including the 125, 85, 55, and 42 kDa surface antigens. The 42 kDa protein is consistently recognized even at dilutions of greater than or equal to 1:16,000.

Example 5-Further Characterization of Proteins

The immunodominant 42 kDa merozoite surface protein was further characterized as an integral membrane protein based on its hydrophobic nature in phase separated TRITON TM X-114 solution. By definition, integral membrane proteins have a hydrophobic domain that allows interaction with the hydrophobic core of the lipid bilayer and with non-ionic detergents. Parasite proteins were metabolically labeled in culture with $^{35}$S-methionine and solubilized in 1% TRITON TM X-114 at 0°–4° C. The antigen preparation was warmed above the detergent's cloud point (20° C.) and separated into aqueous and detergent phases by centrifugation. Immunoprecipitation from each phase and the starting solution shows that the 42 kDa antigen partitions into the detergent phase.

In order to better characterize merozoite surface antigens, the parasite was examined for the ability to incorporate $^3$H-glucosamine and $^3$H-myristic acid into immunoprecipitable proteins. Comigration on a polyacrylamide gel shows that three of the surface labeled proteins (55, 42, and 25 kDa) are glycosylated and the 42 kDa glycoprotein is myristylated.

Example 6-Further Studies on Immunogenicity

Antiserum C151, which was used for immunoprecipitations, was collected from a spleen-intact cow 60 days after experimental infection with a cryopreserved Mexico isolate blood stabilate of B. bovis. B. bovis proteins were metabolically labeled in microaerophilus stationary-phase culture by incubation in methionine-deficient medium for 18 to 24 hr with 10 uCi of [$^{35}$S]methionine per ml. Antiserum C151 immunoprecipitated homologous Mexico isolate proteins biosynthetically labeled with [$^{35}$S]methionine with molecular weights ranging from 14,500 to greater than 200,000. Serial dilution of this antiserum resulted in a decrease in the number of proteins recognized. Proteins reactive with serum diluted 1:40 had relative molecular weights of 145,000, 120,000 (doublet), and 42,000, while the 42,000 molecular weight protein was still recognized by serum diluted 1:80.

Example 7-B. bovis Proteins with Isolate-Common Epitopes

Five different antisera obtained from cattle after recovery from acute infection with B. bovis in Honduras were able to immunoprecipitate most of the Mexico isolate B. bovis proteins precipitated by C151 antiserum. The 120,000 and 42,000 molecular weight proteins recognized by 1:40 dilutions of C151 antiserum were also recognized by 1:25 dilutions of the Honduran antisera.

Example 8-B. bovis Proteins with Species-Common Epitopes

Antiserum B85 was collected from a spleen-intact calf 25 days after experimental infection with a cryopreserved Mexico isolate of B. bigemina. This antiserum, which had an indirect fluorescent-antibody titer of 1:1,600 against the Mexico B. bigemina isolate, reacted with the Mexico B. bovis isolate at a titer of 1:64. Antiserum C151 (anti-B. bovis Mexico isolate) had indirect fluorescent-antibody titers of 1:5,120 and 1:640 against B. bovis and B. bigemina, respectively. Antiserum B85 immunoprecipitated eight [$^{35}$S]methionine-radiolabled proteins of B. bovis. Four of the eight B. bovis proteins immunoprecipitated by B85 antiserum (120,000, 59,000, 53,000, and 19,000 molecular weight) also had isolate-common epitopes. In addition, the 120,000 molecular weight protein was one of the proteins recognized by C151 serum antibodies diluted 1:40.

Example 9-Identification of Monoclonal Antibodies

Using similar techniques, additional MoAbs specific for surface-exposed epitopes on live merozoites were identified. All of the identified MoAbs are listed in Table 1. The MoAbs reacted with the outer surface of culture- or stabilate-derived merozoites in either a punctate (restricted to a discrete region on the merozoite surface) or a homogenous (over the entire surface of the merozoite) pattern when examined by IFA-live.

TABLE 1

Monoclonal antibodies generated against surface proteins on merozoites of Babesia bovis.

| MoAb | Isotype | MW of Reactive Protein ($\times 10^{-3}$ kd) |
|---|---|---|
| 23.8.34.24 | G$_3$ | 225 |
| BABB75 | G$_{2b}$ | 60 |
| MBOC79 | G$_1$ | 60 |
| 23.53.156 | G$_{2a}$ | 60 |
| 23.38.120.8 | G$_1$ | 60 |
| 23.70.174.83 | G$_1$ | 44 |
| BABB35A$_4$ | G$_{2a}$ | 42 |
| 23.3.16 | G$_1$ | 42 |
| 23.10.36 | G$_{2b}$ | 42 |
| 23.28.57.108 | G$_{2a}$ | 16 |
| BABB90C$_4$ | G$_1$ | 85 |
| BABB93A$_1$ | G$_{2a}$ | 145 |

All MoAbs reacted with merozoite antigen in dot immunoassay and allowed detection of specific surface-exposed determinants in preparations of 10$^5$ lysed merozoites. The parasite specificity of these MoAb-reactive determinants was confirmed by immunoprecipitation of metabolically-radiolabeled parasite proteins of M$_r$ 16 kDa, 42 kDa, 44 kDa, 60 kDa, and 225 kDa. These proteins have been designated Bo16, Bo42, Bo44, Bo60, and Bo225, respectively. Bo225 was routinely visualized as a tightly spaced doublet when immunoprecipitated with MoAb 23.8.34.24.

Seven monoclonal antibodies and the Mexico isolate of B. bovis have been deposited with the American Type Culture Collection (ATCC), 12301 Parklawn Drive, Rockville, Md. 20852 USA. The cultures have been assigned the following accession numbers by the repository:

| Biological Material | Deposit number | Deposit date |
|---|---|---|
| MoAb 23.38.120.8 | HB 10111 | May 2, 1989 |
| MoAb BABB93A$_1$ | HB 10112 | May 2, 1989 |
| MoAb 23.8.34.24 | HB 10113 | May 2, 1989 |
| MoAb 23.70.174.83 | HB 10114 | May 2, 1989 |
| MoAb BABB35A$_4$ | HB 10115 | May 2, 1989 |
| MoAb 23.28.57.108 | HB 10377 | March 7, 1990 |
| MoAb BABB90C$_4$ | HB 10117 | May 2, 1989 |
| Babesia bovis, Mexico Isolate | ATCC 40601 | May 3, 1989 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

Example 10-Construction of a Lambda-gt11 Expression Library

Partially purified and viable merozoites free from contaminating bovine leukocytes were obtained from frozen stabilates. Merozoites ($1.4 \times 10^8$ 6-CFDA-positive) were lysed in 10 mM Tris, 1 mM EDTA (TE buffer, pH 7.4) containing 2% SDS, and the suspension was treated with DNAse-free RNAse A (100 ug/ml) followed by Proteinase K (100 ug/ml). Genomic DNA was isolated from the suspension by sequential phenol, phenol/chloroform, chloroform, and ether extractions followed by ethanol precipitation at 0°-4° C. in the presence of 2M ammonium acetate. The DNA pellet was washed once with 70% ethanol, lyophilized, resuspended in TE buffer and stored at 4° C. The concentration and purity of the DNA were assessed by spectrophotometry and agarose gel electrophoresis. The DNA was sheared into fragments of between 4-8 kb by repeated passages through a 25 gauge hypodermic needle (Young, R. A., B. R. Bloom, C. M. Grosskinsky, J. Ivanyi, D. Thomas, and R. W. Davis [1985] Proc. Natl. Acad. Sci. USA 82:2583-2587) and the fragments prepared for ligation into the EcoRI site of the lambda-gt11 expression vector (Promega Biotec, Madison, Wis.).

First, fragements were methylated with EcoRI methylase (Promega Biotec) and blunt-ended using the large fragment of *E. coli* DNA polymerase I (Klenow Fragment, Bethesda Research Laboratories, Gaithersburg, Md.). EcoRI linkers (BRL, Gaithersburg, Md.), end-labeled with $^{32}P$ transferred from 5'-[gamma-$^{32}P$]ATP in a kinase reaction (Huyhn et al., 1985), were ligated to fragment termini using T4 DNA ligase (Bethesda Research Laboratories). Free linkers were separated from fragments with EcoRI termini by size fractionation on a Sephacryl S-400 column (Pharmacia AB, Uppsala, Sweden) following digestion of the reaction mixture with EcoRI endonuclease.

Fractions containing fragments with EcoRI cohesive termini but free of nonligated linkers were pooled, butanol-extracted to reduce volume, extracted twice with ether, ethanol-precipitated, lyophilized, and resuspended in TE buffer. Fragments were then ligated into the EcoRI site of the lambda-gt11 expression vector which resulted in the insertion of parasite DNA into the β-galactosidase structural gene (lacZ) of the bacteriophage (Young, R. A. and R. W. Davis [1983] Proc. Natl. Acad. Sci. USA 80:1194-1198). Ligated DNA was packaged into gamma phage heads (Gigapack Gold Packaging Extract, Stratagene Cloning Systems, San Diego, Calif.) and the resultant library was amplified in *E. coli* strain Y1090 as described previously (Young and Davis, 1983). The amplified library was stored in sterile SM buffer (0.1M NaCl, 8 mM MgSO$_4$.7H$_2$O, 50 mM Tris [pH 7.5], 2% gelatin) at 4° C.

Example 11-Identification of Recombinant Phage Expressing Parasite Surface-Exposed Proteins Recombinant phage expressing proteins with surface-exposed epitopes were identified by immunoscreening plaques with MoAbs. Enough recombinant phage to give $10^5$ plaque forming units (pfu)/150 mm diameter petri dish were used to infect *E. coli* host Y1090 by incubation at 37° C. for 20 min in LB medium. Infected cells were added to LB top agar (55° C.) containing 100 ug/ml ampicillin and 10 mM MgCl$_2$ and plated out on 150 mm diameter LB agar plates. Plates were incubated at 42° C. for 4 hr to allow plaque formation without concomitant expression of fusion protein. LacZ-directed gene expression was then switched on by overlaying each plate with a dry nitrocellulose filter saturated previously with 10 mM IPTG and incubating the plates at 37° C. for 8-10 hr. After incubation, nitrocellulose filters with bound proteins were marked, removed from the plates, and processed as described previously for dot blot immunoassay. Single plaques expressing recombinant surface epitopes of interest were identified by autoradiography, picked from plates, and rescreened and picked three more times to insure purity of the recombinant phage, stability of the DNA insert, and reliability of recombinant protein expression. Other hosts, such as Salmonella, can be transformed by suitable procedures well known to those in the art.

Approximately $4.2 \times 10^6$ recombinant plaques were screened with MoAbs listed in Table 1. Two recombinant clones (lambda-Bo44-15, lambda-Bo44-16) were identified that express a recombinant protein that reacts with MoAb 23.70.174.83 (anti-Bo44) and two (lambda-Bo220-1 and lambda-Bo220-2) that express a recombinant protein that reacts with MoAb 23.8.34.24 (anti-Bo225). When lambda-Bo44-15 and lambda-Bo44-16 were digested with EcoRI, inserts (Bo44-15, Bo44-16) of 1.25 kb were visualized for each recombinant clone. IPTG-induced lysogen preparations of lambda-Bo44-15 consistently produced stronger signals in dot blot immunoassay than did lambda-Bo44-16, and for this reason, lambda-Bo44-15 was chosen for further analysis and use in immunization trials.

Example 12-Induction of Recombinant Proteins with IPTG

*E. coli* host strain Y1089 was lysogenized with lambda-gt11 (control) and each of the recombinant clones using standard procedures (Huyhn, T. V., R. A. Young, and R. W. Davis [1985] "Constructing and Screening cDNA Libraries in lambda-gt10 and lambda-gt11," *DNA Cloning, Vol. 1: A Practical Approach* [Glover, D. M., ed.], pp. 49-78, IRL Press, Washington, D.C.). Lysogenized bacteria were examined by dot blot immunoassay in order to determine the ability of clones to produce recombinant protein after induction with IPTG. Each of the recombinant clones, lambda-gt11-infected *E. coli* Y1089, and noninfected Y1089 controls were grown at room temperature to OD$_{600}$=0.8-1.2. At this time, an aliquot was removed, centrifuged, and lysed with lysis buffer (1% NP-40). The remaining cells were heated rapidly to 42°-45° C. for 20 min, IPTG was added to 10 mM, and the cells were incubated in a shaking incubator at 37° C. for 1-2 hr to induce protein expression. After incubation, cell cultures were adjusted by addition of LB medium to their OD$_{600}$ prior to addition of IPTG. At this time, an aliquot was removed, centrifuged, and the pellet lysed in lysis buffer. Three ul aliquots of pre- and post-induced bacterial lysates were spotted onto nitrocellulose in triplicate and probed with MoAbs specific for surface proteins or an irrelevant MoAb control (CAEV 4Al) in dot blot immunoassays. Crude lysates of bacteria producing recombinant protein were prepared and stored at $-20°$ C. or $-70°$ C. until use.

Dot blot and Western blot analysis of lysates of bacteria lysogenized with lambda-Bo44-15 confirmed the inducibility of rBo44-15 with IPTG and its expression as a $\beta$-galactosidase fusion protein. rBo44-15 was visible as a doublet of $M_r$ 150 kDa and 165 kDa in Western blots of IPTG-induced preparations probed with MoAb 23.70.174.83. In contrast, rBo44-15 was visible as a single band (165 kDa) in Western blots of identical antigen preparations probed with anti-$\beta$-galactosidase. Western blots of lambda-Bo44-15 lysogen preparations probed with an irrelevant IgG$_1$ control MoAb (5.90.1) showed no reactivity, thus confirming the specificity of reaction observed with MoAb 23.70.174.83.

Example 13-Purification of Recombinant Proteins

MoAb 23.70.174.83 was purified from ascitic fluid by ammonium sulfate precipitation and DEAE cellulose chromatography and then coupled to Sepharose 4B for immunoaffinity purification of rBo44-15. Solubilized and sonicated rBo44-15 lysogen preparations were applied to the affinity column, the column was washed repeatedly, then adherent recombinant protein was eluted with 0.1M diethylamine (pH 11.5) containing 0.5% deoxycholate. Elutes were collected directly into 1M Tris (pH 8.5) then dialyzed against PBS to remove detergents. Aliquots of partially purified protein preparations were boiled for 10 min in SDS sample buffer, subjected to SDS-PAGE, silver stained and examined by Western blot immunoassay to verify the presence and purity of recombinant protein. Total protein concentration of the preparations was determined using a bicinchoninic acid protein assay (Pierce Chemical Co.).

Partially purified rBo44-15 from affinity column chromatography contained several high $M_r$ proteins ranging from approximately 94 Kd to >165 Kd as well as several lower $M_r$ proteins ranging from 26 Kd to 50 Kd. Western blot analysis of column-purified protein preparations revealed two major bands of reactivity at $M_r$ 165 Kd and 150 Kd that correspond to two major bands present in silver-stained gels. In addition, several bands of lower $M_r$ (26-31 Kd) were observed in Western blots of affinity-purified recombinant protein that were not observed in Western blots of solubilized lysogen preparations prior to affinity purification. These data indicate that immunoaffinity chromatography results in partial degradation of the recombinant molecule without a concomitant loss of integrity of the MoAb-reactive epitope.

Example 14-Confirmation of the Presence of Surface-Exposed Epitopes on Recombinant Molecules Five Holstein-Freisian bull calves were each immunized intramuscularly (i.m.) with 100-125 ug of affinity column-purified recombinant protein in Freund's complete adjuvant, followed by four to five additional immunizations at three week intervals of recombinant protein in Freund's incomplete adjuvant. Control calves were immunized similarly with 100 ug ovalbumin. Within one week after the last immunization, calves were bled and their sera heat-inactivated and examined by IFA-live (Goff et al., 1988) to confirm the presence of antibodies to surface-exposed epitopes on merozoites. Hyperimmune bovine serum (KLK C151) and preimmune sera were used as positive and negative controls, respectively. Sera from calves immunized with either rBo44-15 or ovalbumin were used to immunoprecipitate metabolically radiolabeled merozoited proteins (McElwain et al., 1987) in order to verify the specificity of the antibody response.

Antibody titers in serum from calves immunized with partially purified rBo44-15 varied from $10^{-2}$ to $10^{-5}$ as evidenced by IFA-live. In contrast, preimmune serum (B452-pre) and serum from ovalbumin-immunized calves showed reactivity with live merozoites at dilutions of $10^{-1}$ and $10^{-2}$, respectively. Antibody in all nondiluted sera or in low serum dilutions ($10^{-1}$, $10^{-2}$) bound to erythrocyte ghosts (infected and noninfected) as well as merozoites within ghosts.

Example 15-Methods and Materials for Construction of DNA Probe (a) Parasites and DNA Isolation Strains of parasites used in this study include a Mexico (M) and Australia (S strain) isolate of *B. bovis* and a Mexico isolate of *B. bigemina*. *Babesia bovis* (M) DNA for both the genomic library preparation and analysis of clones was derived from infected bovine erythrocyte cultures washed three times in phosphate buffered saline (PBS), pH 7.2, followed each time by centrifugation at 400 xg. *Babesia bovis* (S) and *B. bigemina* DNA was similarly derived from infected calf blood depleted of buffy coats by three washes in PBS. Infected erythrocytes for isolates were differentially lysed in nine volumes of 0.42% NaCl, infected ghosts were pelleted at 400 xg, lysed in 5 volumes of 10 mM Tris-HCl (pH 7.5), 10 mM ethylenediaminetetraacetic acid (EDTA), 100 mM NaCl, and 1% sodium dodecyl sulfate (SDS), incubated 16 hr with proteinase K (100 ug/ml), extracted with phenol:chloroform:isoamyl alcohol (24:24:1). DNA in the aqueous phase was spooled after addition of 2 volumes of cold ethanol, spooled DNA was dried and resuspended in 10 mM Tris-HCl (pH 7.4) and 1 mM EDTA (TE), treated with RNases A and Tl (15 ug/ml, 15 units/ml, respectively). The solution was reextracted, spooled, dried, and resuspended in TE for use.

To obtain bovine leukocyte DNA, cells in the buffy coat of uninfected blood were processed similar to infected erythrocytes.

(b) Identification and Isolation of Recombinant *B. bovis* DNA

The preparation of the genomic library has been described. Briefly, *B. bovis* genomic DNA was sheared through a 26 gauge needle to sizes ranging from c4-8 Kb, methylated with EcoRI methylase, EcoRI linkers were added, DNA restricted with EcoRI and separated from digested linkers on sephacryl S-400 (Pharmacia), and DNA ligated into EcoRI digested and dephosphorylated arms of lambda-gt11. Recombinant phage were amplified in *Escherichia coli* strain Y1089 (Stratagene).

DNA from phage plaques was adsorbed onto nitrocellulose and replicate filters were differentially hybridized to nick translated DNA (2X $10^6$ cpm/ml) from either *B. bovis* (M) or *B. bigemina* in 6X SSPE (1X SSPE:150 mM NaCl, 10 mM NaH$_2$PO$_4$, 1 mM EDTA, pH 7.4), 100 ug/ml denatured salmon sperm DNA, and 1% SDS at 65° C. for 16 hr. Filters were washed twice in 2X SSPE and 1% SDS at room temperature for 20 min, and twice in 0.1X SSPE and 0.1% SDS at 65° C. for 20 min. Dried filters were autoradiographed at −70° C. Recombinant phage hybridizing to *B. bovis* (M) but not detectably to *B. bigemina* DNA were purified through 3 rounds of rescreening and isolated for further analysis. Based on characteristics of hybridization to *B. bovis* (M) genomic DNA, inserts from some recombinants were cloned into plasmid pBS+ (Stratagene) to facilitate their analysis.

(c) Southern and Dot Blot Assays

To investigate the genomic organization of candidate probe sequences, restriction fragments were separated electrophoretically on 0.7% agarose gels and transferred to nylon filters. Filters were then hybridized, as described above, in the presence of 10% dextran sulfate, to lambda-gt11 recombinant DNA or preparatively isolated insert DNA that was radioactively labeled. Final wash stringency was either 65° C. or 50° C., as indicated.

For dot blot analysis, DNA extracted as described above was spotted onto nylon membranes. Membranes were dried at room temperature, saturated with 0.5M NaOH and 1.5M NaCl, neutralized in 1M ammonium acetate and 0.02M NaOH, rinsed in 6X SSPE, and vacuum-dried at 80° C. for 1 hr. Hybridization conditions were similar to those used for Southern blots. Sensitivity of probe sequences was determined for autoradiograms exposed to hybridization filters for approximately 16 hr at −70° C. using an intensifying screen.

Example 16-Candidate DNA Probes for Detecting *Babesia bovis* in Infected Ticks and Cattle DNA-DNA hybridization assays (DNA probes) are based on the fact that single-stranded DNA will reanneal only with a complementary strand of DNA whose sequence is homologous. DNA probes have been used as a means of detecting various infectious agents, and some are now used routinely in clinical microbiology laboratories. The identification of DNA sequences of Babesia spp. makes it possible to create DNA probes for the identification of these species. Therefore, one application of the identification and isolation of genomic sequences which encode babesial antigens is the use of the DNA fragments as DNA probes.

The lambda-gt11 genomic DNA library of *Babesia bovis* was screened to identify DNA probe candidates for direct detection of the parasite in blood or ticks infected with the parasite. Two sequences (lambda-Bo6 and lambda-Bo25) demonstrated superior sensitivity and were analyzed in more detail. The insert size of lambda-Bo6 is 2.75 kilobase pairs (kb). An accurate estimate of the lambda-Bo25 insert was not possible since one of the EcoRI insert sites was lost during cloning. However, digestion of lambda-Bo25 with EcoRI and KpnI produces a fragment of 2.2 kb which is specific to this clone compared to wild type lambda-gt11. Since the KpnI site in lambda-gt11 occurs approximately 1 kb from the EcoRI cloning site, a minimum estimated size of the insert is 1.2 kb.

Inserts from the lambda clones were excised with EcoRI (lambda-Bo6) or SstI and KpnI (lambda-Bo25) and cloned into the plasmid BS+ (Stratagene), producing the two clones pBo6 and pBo25. Insert fragments preparatively isolated from these plasmid clones were radioactively labeled and used in dot and Southern blot analyses.

Neither sequence hybridized detectably to bovine DNA. pBo6 detected 100 pg of both a Mexico and an Australia isolate of *B. bovis*, but pBo6 also detects 1.0 ng of *B. bigemina* DNA under identical conditions. A unique characteristic of pBo6 is that it hybridizes to a 7.4 kilobase band in uncut genomic DNA of both *B. bovis* and *B. bigemina*. Similarity of restriction enzyme patterns of the pBo6 sequence in genomic DNA from both geographic isolates suggests that this sequence is well conserved between geographic isolates of *B. bovis*. Thus, this sequence is a candidate DNA probe for detecting *B. bovis* infections in cattle and ticks.

pBo25 exhibited no detectable hybridization to bovine or *B. bigemina* DNA. This sequence detected 100 pg of homologous Mexico isolate DNA, but under identical conditions the sensitivity was reduced to 1 ng for Australia isolate DNA. Restriction enzyme analysis of the pBo25 sequence showed major differences in the number, size, and intensity of bands between the two *B. bovis* geographic isolates tested. Thus, this sequence can distinguish geographic isolates of *B. bovis*.

Example 17-Labeling of DNA Probe

In order to facilitate detection, DNA probes can be labeled in a variety of ways. For example, for biotin labelling, the DNA fragment preparation is adjusted to a concentration of 1 mg/ml (TE) and is mixed with photo-activatable biotin (PAB) at a ratio of 1:3 (DNA:-PAB) in a 1.5 ml Eppendorf tube. The tube is placed in an ice bath 10 cm below a 275 W (GE RSM) sunlamp and the DNA+ PAB is irradiated for 15 min. The DNA solution is then mixed with an equal volume of 0.1M Tris-Cl (pH 9.0) and the volume adjusted to 100 ul with $H_2O$. The unincorporated PAB is extracted from the DNA by the addition of an equal volume of 2-butanol, vortexing, centrifuging briefly, and withdrawing the lower aqueous phase with a Pipetman. The extraction can be repeated to remove any traces of unbound PAB. 3M NaOAc (pH 5.6) is added to the DNA solution to a final concentration of 0.3M and the labeled DNA is precipitated by the addition of 3 volumes of ethanol.

After the sample is cooled at −70° C. for 15 min, the precipitated DNA is recovered by centrifugation for 10 min. The DNA pellet is dissolved in 10 mM Tris (pH 7.9) and 0.1 mM EDTA. The labeled probe DNA remains stable for 1 year if stored at −20° C.

A non-radioactive method of labeling the DNA probes may be desirable because: 1) the photoactivatable reactions are simple and rapid, 2) the sensitivity is as high as $^{32}P$-labeled probes, 3) the PAB-labeled probes have a long storage life, 4) these probes are relatively inexpensive, and 5) detection of bound probes is by simple colorimetric methods. The radioactive labeling of probes requires the use of 32P, which has a very short half-life (14 days) and is thus unstable and expensive. The use of radioactive probes would be limited because of cost, the dangers of radioactivity, strict requirements for disposal, and the need for licensing.

However, if for some reason the biotin-HRP method of labeling is not acceptable, the DNA fragments can be labeled with [gamma-P] 32 deoxy CTP by standard nick translation methods.

Example 18-Description of Recombinant DNA Sequence from *B. bovis* that Encodes an Immunoreactive Epitope Located on the Surface of Merozoites The cloned insert DNA was excised from the lambda-gt11 vector and recloned into the plasmid BS+ (Stratagene), producing the clone pBo44-15. DNA templates for sequencing the insert of pBo44-15 were obtained by creating deletion libraries of this clone using exonuclease III and mungbean nuclease. A different deletion library was obtained starting at each end of the clone, which allowed sequencing of both strands of the insert DNA. The DNA sequence was obtained using the Sanger dideoxy method.

The sequence of Bo44-15 insert DNA is shown in FIG. 1A. The insert is 1235 base pairs long. The amino acid sequence shown represents the one long open reading frame identified in the sequence. The open reading frame begins at position 1 and encodes a stop codon (TAA) beginning at position 568. This reading frame is in correct register for expression as a fusion protein of β-galactosidase in lambda-gt11, provided the clone is in the correct orientation. A notable feature of this open reading frame is that it would encode a 24 amino acid sequence beginning at AA position 85 which is tandemly repeated beginning at AA position 109. Comparison of these two putative repeats shows only two positions that differ between the repeats as shown below:

```
85  PQRPAETQQTQDSAAPSTPAAPSP 108
109 PQRPAETQQTQDSTAPGTPAAPSP 132
                  *  *
```

Numbers represent the beginning and ending amino acid position in the open reading frame for each repeat. Letters are the single letter code for amino acids. Asterisks below the aligned repeats indicate amino acid differences between the two repeats.

The potential significance of the repeat amino acid sequence is that such repeats are often immunodominant epitopes in surface proteins from a variety of other protozoan parasites, and they induce antibodies that protect against the diseases.

The DNA sequences coding for two other of the *B. bovis* proteins have also been discovered. The DNA sequence for the *B. bovis* surface proteins of 42 kDA and 60 kDA are shown in FIGS. 2A and 3-1 through 3-2, respectively. These sequences, or portions of the sequences, can be used as DNA probes as described in Examples 16 and 17. Also, the proteins produced from cells transformed with these sequences, or portions of these sequences, can be used for vaccines or in the preparation of monoclonal antibodies as described in the examples which follow.

The procedure for obtaining these sequences are described below: *B. bovis* cDNA Expression Library. Erthrocytes from asynchronous *B. bovis*-infected blood cultures were washed three times in Puck's saline G and stored frozen in liquid nitrogen. Cells were thawed in lysis buffer containing 0.2M NaNl, 0.2M Tris-HCl pH 7.5, 1.5 mM $MgCl_2$, 2% SDS (w/v), and 200 μg/ml Proteinase K and then incubated in lysis buffer at 46° C. for two hours (Bradley, J. E., G. A. Bishop, T. St. John, and J. A. Frelinger [1988] Biotechniques 6:114–116). The NaCl concentration of the lysate was adjusted to 0.5M and poly [A+] RNA was isolated by batch adsorption with oligo(dT) cellulose (Bradley et al., supra). DNA eluted with 0.01M Tris-HCl pH 7.5 was used to prepare a blood stage cDNA library in Lambda ZAP II (Stratagene, La, Jolla, Calif. U.S.A.) (Short, J. M., J. M. Fernandez, J. A. Sorge, and W. D. Huse [1988] Nucl. Acids Res. 16:7583–7600) by a modified Gubler and Hoffman method using EcoRI adapters (Pharmacia LKB, Piscataway, N.J. U.S.A.) (Gubler, U., and B. Hoffman [1983] Gene 25:263–269). The cloned insert in plaque purified lambda phage was subcloned into Bluescript SK(-) phagemid using the in vivo excision capabilities of Lambda ZAP II (Short et al., supra).

Immunoscreening. Plaque lifts ont isopropyl thiogalacto-pyranoside soaked nitrocellulose were screened using monospecific rabbit anti-Bv42 antisera (R-914) followed by $^{125}$I-Protein A and autoradiography, or with anti-Bv60 monoclonal antibody (23.38.120.8) followed by rabbit anti-murine immunoglobulin, $^{125}$I-Protein A and autoradiography (Young, R. A., and R. w. Davis [1983] Proc. Natl. Acad. Sci. U.S.A. 80:1194–1198; Reducker, D. W. Jasmer, W. L. Goff, L. E. Perryman, W. C. Davis, and T. C. Mcguire [1989] Mol. Biochem. Parasitol. 35:239–248). Rabbit R-914 had been immunized with native Bv42 protein immunoaffinity purified using $BABB35A_4$, a previously monoclonal antibody (Goff, W. L., W. C. Davis, G. H. Palmer, T. E. McElwain, W. C. Johnson, J. F. Bailey, and T. C. McGuire [1988] Infect. Immun. 56:2363–2368). Positive Bv42 plaques were tested for reactivity with monoclonal antibodies that recognize a Bv42 surface exposed epitope (Goff et al., supra; Reducker et al., supra) as well as an isotype control monoclonal antibody and normal rabbit serum. Recombinant phagemid excised from positive, plaque purified lambda phage was tested for expression by a similar method using colony lifts from transformed, ampicillin resistant *E. coli*(XL1-Blue strain) (Young and Davis, supra).

Restriction Enzyme Digestion. Lambda rBv42 phagemid DNA was isolated from bacteria by anion exchange chromatography (Qiagen Inc., Studio City, Calif.) and restriction enzyme digested by standard methods (Maniatis, T., E. F. Fritsch, and J. Sambrook [1982] *Molecular Cloning: A Laboratory Manual.* Cold Spring Harbor Laboratories, Cold Spring Harbor, N.Y., 545 pp.)

Example 19-Vaccines

Vaccines may be produced from the polypeptides expressed by the parasites themselves or by cells which have been transformed with DNA fragments from Babesia. By introducing these polypeptides, along with a pharmacologically suitable vehicle or adjuvant, into the animal host, that host can be induced to generate immunological protection against Babesia. The preparation of such a vaccine composition is within the skill of one trained in the medical and immunological sciences. Vaccines may utilize entire polypeptides or epitopes with immunological activity.

Example 20-Monoclonal Antibodies

Appropriate mice can be immunized with antigens of, or cells expressing antigens of, Babesia. The antigens used for this immunization can be those which are identified and described in the previous examples. The techniques employed to accomplish this immunization procedure are familiar to those skilled in this art. The spleens can then be removed from the immunized mice and the cells therefrom fused to SP-2 myeloma cells using polyethylene glycol. The desired hybrid cells can then be selected by adding hypozanthine-aminopterinthymidine to the medium. The surviving cells can then be tested for antibody production. The testing for antibody production can be accomplished using IFA, ELISA, immunoblot, and/or immunoprecipitation procedures.

Example 21- Detection of Babesia Antigens

The monoclonal antibodies, such as those produced by the procedure just described or those disclosed in Examples 1 and 9, can be used to test for the presence of Babesia antigens in a sample of biological fluid. Other monoclonal antibodies to Babesia antigens can also be used. The testing procedure involves contacting the biological fluid with a composition containing one or more of the monoclonal antibodies. If Babesia antigens are present in the biological fluid, then a reaction will occur and this reaction can be detected and quantified by fluorescence or other means.

Example 22-Detection of Anti-Babesia Antibodies

Anti-Babesia antibodies can be detected in a fluid sample from a bovine suspected of containing these antibodies by performing ELISA procedures on the clinical samples. Generalized ELISA procedures are well known to those skilled in the art. The ELISA procedures or other simple diagnostic procedures of the subject invention could utilize as antigens, for example, whole cell or cell lysate using recombinant microorganisms which express Babesia antigens.

When the biological sample is contacted with the whole cell or cell lysate microorganisms, this contacting is done under conditions which will promote antigen/antibody immunocomplex formation between antigens expressed by the microorganism and antibodies present in the sample. The resulting immunocomplex can be readily detected utilizing standard labeling procedures.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated DNA sequence as set forth in FIGS. 3-1 through 3-2.
2. An isolated DNA sequence coding for the polypeptide shown in FIG. 4.
3. A microorganism transformed with the DNA sequence shown in FIGS. 3-1 through 3-2.
4. A microorganism, according to claim 3, wherein said microorganism is an *Escherichia cole* or Salmonella spp.

* * * * *

UNITED STATES PATENT AND TRADEMARK OFFICE
CERTIFICATE OF CORRECTION

PATENT NO.    :    5,171,685

DATED         :    December 15, 1992

INVENTOR(S)   :    Terry F. McElwain *et al.*

It is certified that error appears in the above-identified patent and that said Letters Patent is hereby corrected as shown below:

Column 1:     line 3: <u>omitted</u> should read --This invention was made with government support under USAID Grant Nos. DAN-4178-A-00-7056-00, DHR-5600-G-00-1035-00, and HRN-5600-G-00-2034-00; USDA Grant Nos. NRICGP-92-37204-8180 and 86-CRSR-2-2842; and USDA-BARD Grant Nos. US-1855-90RC and US-1080-86. The government has certain rights in this invention.--

Column 3:     line 60: "lambdagt11" should read --lambda-gt11--.

Column 4:     line 14: "lambda-BO6" should read --lambda-Bo6--.

Column 8:     line 29: "lambdagt11" should read --lambda-gt11--.

Column 13:    line 39: "fragements" should read --fragments--.

Column 14:    line 51: "DNA Cloning" should read --In: *DNA Cloning*--.

Column 19:    line 60: "NaNl" should read --NaCl--.

Column 20:    line 11: "lifts ont" should read --lifts onto--; line 19: "Reducker, D.W. Jasmer" should read --Reduker, D.W., D.P. Jasmer; line 23: "previously monoclonal" should read --previously described monoclonal--; line 25: "T.E. McElwain" should read --T.F. McElwain--.

Column 22:    line 25: "*Escherichia cole*" should read --*Escherichia coli*--.

Signed and Sealed this

Seventh Day of November, 1995

BRUCE LEHMAN

*Attest:*

*Attesting Officer*        Commissioner of Patents and Trademarks